United States Patent [19]

Ueda et al.

[11] 4,094,870
[45] June 13, 1978

[54] 2-SUBSTITUTED THIO-1,4-BENZODIAZEPINE DERIVATIVES

[75] Inventors: Ikuo Ueda, Yao; Masaaki Matsuo, Toyonaka, both of Japan

[73] Assignee: Fujisawa Pharmaceutical Co., Ltd., Osaka, Japan

[21] Appl. No.: 732,929

[22] Filed: Oct. 15, 1976

Related U.S. Application Data

[63] Continuation-in-part of Ser. No. 559,886, Mar. 19, 1975, abandoned.

[30] Foreign Application Priority Data

Mar. 20, 1974 Japan ................................ 49-31905

[51] Int. Cl.² .................. A61K 31/395; C07D 243/22
[52] U.S. Cl. .......................... 260/239 BD; 260/239 B; 260/293.59; 260/326.81; 424/244; 260/243.3
[58] Field of Search ................ 260/239 BD

[56] References Cited

U.S. PATENT DOCUMENTS

| 3,481,921 | 12/1969 | Field et al. ............ 260/239 BD |
| 3,856,787 | 12/1974 | Steinman ............... 260/239 BD |

FOREIGN PATENT DOCUMENTS

| 240,373 | 10/1964 | Austria ................ 260/239 BD |
| 2,511,898 | 9/1975 | Germany ............... 260/239 BD |
| 6,614,923 | 4/1967 | Netherlands ........... 260/239 BD |

Primary Examiner—Donald G. Daus
Assistant Examiner—James H. Turnipseed
Attorney, Agent, or Firm—Dayton R. Stemple, Jr.

[57] ABSTRACT

2-substituted thio-1,4-benzodiazepine derivatives having medicinal use of the general formula

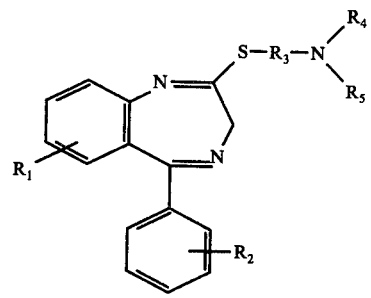

wherein $R_1$ and $R_2$ individually signify hydrogen atom or a halogen atom, or a nitro, amino, hydroxy, cyano, alkyl, haloalkyl, alkoxy, alkylthio, alkanesulfinyl, alkanesulfonyl, alkanoylamino or dialkylamino group, $R_3$ signifies an alkylene group, and $R_4$ and $R_5$ individually signify hydrogen atom or an alkyl group and, when $R_4$ and $R_5$ are both alkyl groups, said alkyl groups together may form a ring with or without oxygen atom or an imino group, said ring optionally having a substituent or substituents, and its non-toxic pharmaceutically acceptable salts.

21 Claims, No Drawings

2-SUBSTITUTED THIO-1,4-BENZODIAZEPINE DERIVATIVES

RELATED APPLICATION

This application is a continuation-in-part application of our copending application Ser. No. 559,886 filed Mar. 19, 1975, now abandoned.

SUMMARY OF THE INVENTION

This invention relates to a novel class of 2-substituted thio-1,4-benzodiazepine derivatives, and the process for preparing same. This invention further pertains to medicinal use of such 2-substituted thio-1,4-benzodiazepine derivatives.

In one aspect of the present invention, there is provided a novel class of 2-substituted thio-1,4-benzodiazepine derivatives of the general formula

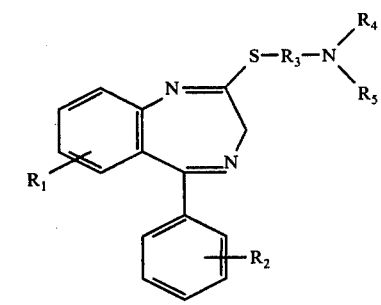

wherein $R_1$ and $R_2$ individually signify hydrogen atom or a halogen atom, or a nitro, amino, hydroxy, cyano, alkyl, haloalkyl, alkoxy, alkylthio, alkanesulfinyl, alkanesulfonyl, alkanoylamino or dialkylamino group, $R_3$ signifies an alkylene group, and $R_4$ and $R_5$ individually signify hydrogen atom or an alkyl group and, when $R_4$ and $R_5$ are both alkyl groups, said alkyl groups together may form a ring with or without oxygen atom or an imino group, said ring optionally having a substituent or substituents, and its non-toxic pharmaceutically acceptable salt.

The term "alkyl group" used in the above and throughout the specification and claims can be understood to mean preferably $C_1$ to $C_{10}$ alkyl groups, and more preferably lower alkyl groups, e.g. $C_1$ to $C_6$-alkyl groups. Similarly, the alkyl and alkane moieties of various groups referred to in connection with the definition for $R_1$ and $R_2$ preferably mean those having one to ten carbon atoms and more preferably mean lower alkyl or lower alkane of one to six carbon atoms. The alkylene group taken for $R_3$ preferably is $C_1$ to $C_{18}$-alkylene group and more preferably is $C_1$ to $C_{10}$-alkylene.

According to a further aspect of the invention, these new 2-substituted thio-1,4-benzodiazepine derivatives as defined above can be obtained by reacting a 1,4-benzodiazepine-2-thione derivative of the general formula

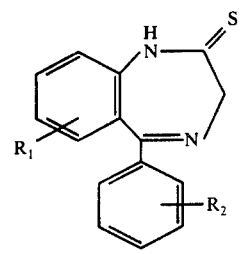

wherein $R_1$ and $R_2$ individually have the same meanings as defined above, with a compound (hereinafter, sometimes referred to as a "S-substitution agent") of the general formula

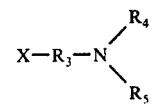

wherein $R_3$, $R_4$ and $R_5$ individually have the same meanings as defined above, and X signifies an acid residue. The reaction which takes place thereby can be schematically shown below:

DETAILED DESCRIPTION

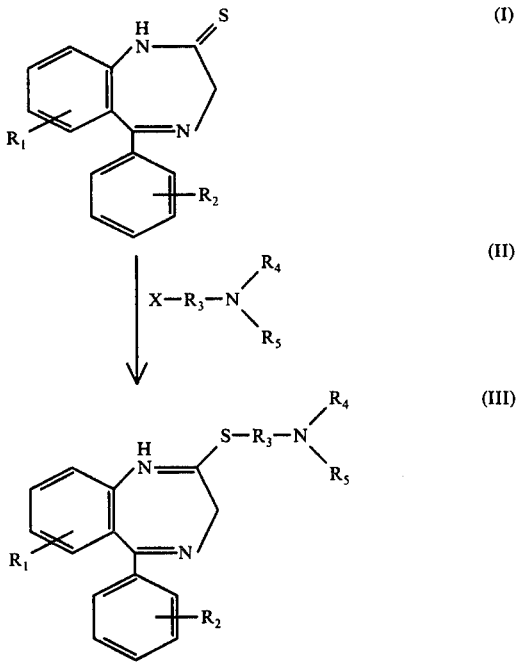

Among the starting materials (I) used in the present invention, for example, 1,3-dihydro-5-phenyl-7-chloro-2H-1,4-benzodiazepine-2-thione is a known compound. This compound may be prepared, for instance, by a process described in Journal of Organic Chemistry, Vol. 29, 231–233 (1964), and the rest of the starting materials (I) may also be prepared in the like manner.

The process of the present invention is carried out by reacting a 1,4-benzodiazepine-2-thione derivative (I) with a S-substitution agent (II). The starting material, 1,4-benzodiazepine-2-thione derivative as used herein is intended to designate those which are represented by the aforesaid general formula (I) and more particularly to mean the compounds of the general formula (I) in which $R_1$ and $R_2$ are individually hydrogen atom, a halogen atom such as fluorine, chlorine or bromine, nitro group, amino group, hydroxy group, cyano group, an alkyl group such as methyl, ethyl, propyl, isopropyl, butyl, isobutyl, tert.-butyl pentyl or hexyl, a haloalkyl group such as chloromethyl, bromomethyl, chloropropyl, 1,2-dichloroethyl or trifluoromethyl, an alkoxy group such as methoxy, ethoxy, propoxy, isopropoxy, butoxy, isobutoxy, tert.-butoxy, pentyloxy or hexyloxy, an alkylthio group such as methylthio, ethylthio, propylthio, isopropylthio, butylthio, isobutylthio, tert.-butylthio, pentylthio or hexylthio, an alkanesulfinyl group such as methanesulfinyl, ethanesulfinyl, propanesulfinyl, isopropanesulfinyl, butanesulfinyl, isobutanesulfinyl, tert.-butanesulfinyl, pentanesulfinyl or hexanesulfinyl, an alkanesulfonyl group such as methanesulfonyl, ethanesulfonyl, propanesulfonyl, isopropanesulfonyl, butanesulfonyl, isobutanesulfonyl, tert.-butanesulfonyl, pentanesulfonyl or hexanesulfonyl, an alkanoylamino group such as acetamido, propionamido, butyramido, isobutyramido, valeramido, pivalamido or octanamido, or a dialkylamino group such as dimethylamino, diethylamino or methylethylamino.

Further, the S-substitution agent used in the present invention is a compound represented by the aforesaid general formula (II) and more particularly the compound is intended to designate those as having said general formula (II) in which X is an acid residue of a halogen acid such as hydrochloric, hydrobromic or hydroiodic acid, p-toluenesulfonic acid, alkylsulfuric acid, benzenesulfonic acid or dialkylcarbamic acid, $R_3$ is a straight or branched chain alkylene group such as methylene, 1-methylmethylene, ethylene, propylene, trimethylene, tetramethylene, pentamethylene, hexamethylene or decamethylene and $R_4$ and $R_5$ are individually hydrogen atom or an alkyl group such as methyl, ethyl, propyl, isopropyl, butyl, isobutyl, tert.-butyl, pentyl or hexyl. In the said general formula (II), when both $R_4$ and $R_5$ are alkyl groups, said alkyl groups together may form a ring with or without oxygen atom or an imino group. In that case where the ring is formed by the said two alkyl groups, there may be present on said ring one or more substituents such as a hydroxy group, alkyl group (e.g. methyl, ethyl, propyl, isopropyl, butyl, isobutyl, tert.-butyl, pentyl or hexyl), phenyl group, or substituted phenyl group having a substituent which does not exert a harmful influence on the reaction, (e.g. a halogen atom such as fluorine, chlorine or bromine, or an alkoxy group such as methoxy, ethoxy, propoxy, isopropoxy, butoxy, isobutoxy, tert.-butoxy, pentyloxy or hexyloxy), and the number of the substituents on said ring may be either one or two or more. Among the

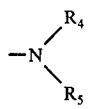

groups, examples of the groups which may be formed by the cyclization of $R_4$ and $R_5$, both being alkyl groups, in the manner mentioned previously include, for example, a 5- to 7-membered saturated heterocyclic group containing at least one nitrogen atom, which may have the substituent(s) mentioned above. Such heterocyclic group may be, in detail, a one or two nitrogen containing 5- to 7-membered saturated heterocyclic group which may have the substituent(s) mentioned above, such as 1-pyrrolidinyl group, piperidino group, 1-piperazinyl group, 1-perhydroazepinyl group, 4-methyl-1-piperazinyl group, 4-(2-methoxyphenyl)-1-piperazinyl group or 4-hydroxy-4-(4-chlorophenyl)-piperidino group; a 6 membered saturated heterocyclic group having one nitrogen atom and another one hetero atom (e.g., oxygen atom), such as morpholino group; and the like.

The reaction of the present invention may also be carried out in the presence of a basic condensing agent. Usable as the condensing agents in the present reaction are inorganic bases such as hydrides, amides, alkoxides and carbonates of such alkali metals as lithium, sodium and potassium, or of such alkaline earth metals as magnesium, calcium and barium, or organic bases such as pyridine, trimethylamine, triethylamine or dimethylaniline.

The intended reaction may ordinarily be carried out in a solvent, for example, water, methanol, ethanol, ether, benzene, toluene, xylene, acetone, dimethylformamide and dimethylsulfoxide. Usable solvents in the reaction are not limited particularly to those enumerated above, and any other solvents may also be usable so long as they do not take part in the reaction. Furthermore, these solvents may also be used in the form of a solvent mixture thereof.

Furthermore, the reaction often proceeds advantageously when a quaternary ammonium compound is used as a catalyst. Examples of such quaternary ammonium compound include, for example, N,N,N',N'-tetramethylpiperazinium dichloride, benzyltriethylammonium chloride, tetramethylammonium chloride, tetraethylammonium bromide and tetrabutylammonium chloride, and any other quaternary ammonium compounds may also be usable so long as they do not exert a harmful influence on the present reaction.

The reaction temperature to be employed may vary depending on the kind of the starting material, 1,4-benzodiazepine-2-thione derivative (I), S-substitution agent (II), basic condensing agent, catalyst and solvent. Ordinarily, however, the reaction is carried out in most cases at room temperature or by heating to a temperature near a boiling point of the solvent employed.

The compound (III) thus formed may be converted, if desired, into the corresponding inorganic acid addition salt such as hydrochloride or sulfate, or into the corresponding organic acid addition salt such as maleate, oxalate, lactate, tartrate, citrate or sulfonate. Such salt formation is serviceable to promote crystallization. However, it is to be noted that a pharmaceutically acceptable salt, which can be obtained when a non-toxic acid is used, is effective and useful as a medicine as well as its parent compound.

Thus, the compounds (III) and their acid addition salts are useful as sedative-hypnotics, anti-convulsants and anti-anxiety agents, and this constitutes a still further aspect of the present invention. In practical administration for a therapeutical purpose, the acid addition salts of the compounds (III) are used in a form of their pharmaceutically acceptable salts.

The compounds (III) and their pharmaceutically acceptable salts can be administered by the conventional methods, the conventional types of unit dosages, or with the conventional pharmaceutical carriers.

Thus, they can be used in the form of pharmaceutical preparations, which contain them in admixture with a pharmaceutical organic or inorganic carrier material suitable for external or parenteral applications. Oral administration by the use of tablets, capsules or in liquid form such as suspensions, solutions or emulsions, is particularly advantageous, and usually administered 3 mg to 60 mg daily by oral administration. The dose, of course, varies according to the age, body weight and the condition of patients, and the like.

The present invention is illustrated below with reference to examples.

EXAMPLE 1

To a solution of 11.4 g of 1,3-dihydro-5-phenyl-7-nitro-2H-1,4-benzodiazepin-2-thione in 140 ml of anhydrous dimethylformamide is added under ice cooling with stirring 3.6 g of sodium hydride (50% oily suspension), and the resulting mixture is stirred at room temperature for 15 minutes. To this mixture is added dropwise at room temperature with stirring 13.2 g of N,N-dimethyl-2-chloroethylamine over a period of about 1 hour, followed by stirring for 1 hour. The reaction mixture is poured into iced water and then extracted with chloroform. The extract is washed with water and dried over magnesium sulfate, and the solvent is then distilled off under reduced pressure. An oily product obtained as the residue is subjected to column chromatography on alumina and eluted from the column with a benzene-chloroform (5:1) eluant. The eluate is concentrated under reduced pressure to obtain an oily 2-(2-dimethylaminoethylthio)-5-phenyl-7-nitro-3H-1,4-benzodiazepine. The oily product thus obtained is treated, according to usual procedure, with maleic acid and then recrystallized from an anhydrous ethanol-acetone mixture to obtain 9.0 g of 2-(2-dimethylaminoethylthio)-5-phenyl-7-nitro-3H-1,4-benzodiazepine maleate, m.p. 131°–134° C.

Elementary analysis: for $C_{19}H_{20}N_4O_2S \cdot C_4H_4O_4$: Calculated: C: 57.01, H: 4.99, N: 11.56; Found: C: 56.97, H: 4.88, N: 11.62.

EXAMPLE 2

To a solution of 6.4 g of 1,3-dihydro-5-(2-chlorophenyl)-7-chloro-2H-1,4-benzodiazepine-2-thione in 50 ml of anhydrous dimethylformamide is added under ice cooling with stirring 1.2 g of sodium hydride (50% oily suspension), and the resulting mixture is stirred at room temperature for 20 minutes. To the mixture is added dropwise 6.6 g of N,N-dimethyl-2-chloroethylamine over a period of 10 minutes, followed by stirring at room temperature for 1 hour. The reaction mixture is poured into iced water and then extracted with chloroform. The extract is water washed and dried over magnesium sulfate, and the solvent is distilled off. An oily product obtained as the residue is subjected to column chromatography on alumina and eluted from the column with benzene. The eluate is concentrated to obtain a crude 2-(2-dimethylaminoethylthio)-5-(2-chlorophenyl)-7-chloro-3H-1,4-benzodiazepine. The crude product thus obtained is treated, according to usual procedure, with maleic acid and then recrystallized from an anhydrous isopropyl alcohol-acetone mixture to obtain 4.8 g of 2-(2-dimethylaminoethylthio)-5-(2-chlorophenyl)-7-chloro-3H-1,4-benzodiazepine maleate, m.p. 140°–142° C.

Elementary analysis: for $C_{19}H_{19}N_3Cl_2S \cdot C_4H_4O_4$: Calculated: C: 54.33, H: 4.56, N: 8.27; Found: C: 54.23, H: 4.57, N: 8.23.

EXAMPLE 3

To a solution of 2.5 g of 1,3-dihydro-5-(2-chlorophenyl)-7-chloro-2H-1,4-benzodiazepine-2-thione in a solvent mixture comprising 10 ml of a 10% aqueous sodium hydroxide solution and 10 ml of methanol is added dropwise under ice cooling with stirring an aqueous solution of 1.7 g of N,N-dimethyl-2-chloroethylamine hydrochloride, and the resulting mixture is stirred at room temperature for 2.5 hours. The reaction mixture is diluted with water and extracted with ethyl acetate. The extract is rinsed with a 5% aqueous sodium hydroxide solution, washed with water and then dried over magnesium sulfate. The solvent is distilled off from the solution to obtain as the residue 2.7 g of an oily 2-(2-dimethylaminoethylthio)-5-(2-chlorophenyl)-7-chloro-3H-1,4-benzodiazepine. The oily product thus obtained is treated, according to usual procedure, with maleic acid and recrystallized from an isopropyl alcohol-acetone mixture to obtain 2.6 g of 2-(2-dimethylaminoethylthio)-5-(2-chlorophenyl)-7-chloro-3H-1,4-benzodiazepine maleate, m.p. 140°–142° C.

EXAMPLE 4

To a solution of 3.2 g of 1,3-dihydro-5-(2-chlorophenyl)-7-chloro-2H-1,4-benzodiazepine-2-thione in a solvent mixture comprising 17 ml of a 10% aqueous potassium hydroxide solution and 1.2 ml of tetrahydrofuran is added at room temperature with stirring 2.16 g of N,N-dimethyl-2-chloroethylamine hydrochloride in its powdery form. The resulting mixture is stirred at room temperature for 3 hours and, thereafter, the reaction mixture is diluted with water and extracted with ethyl acetate. The extract is washed with water, dried and then distilled under reduced pressure to remove the solvent, whereby an oily 2-(2-dimethylaminoethylthio)-5-(2-chlorophenyl)-7-chloro-3H-1,4-benzodiazepine is obtained. The oily product thus obtained is treated, according to usual procedure, with maleic acid and recrystallized from an isopropyl alcohol-acetone mixture to obtain 4.50 g of 2-(2-dimethylaminoethylthio)-5-(2-chlorophenyl)-7-chloro-3H-1,4-benzodiazepine maleate, m.p. 140°–142° C.

EXAMPLE 5

To a solution of 6.4 g of 1,3-dihydro-5-(2-chlorophenyl)-7-chloro-2H-1,4-benzodiazepine-2-thione in 50 ml of anhydrous dimethylformamide is added under cooling with stirring 1,2 g of sodium hydride (50% oily suspension), and the resulting mixture is stirred at room temperature for 20 minutes. To the mixture is added dropwise 7.6 g of N,N-dimethyl-3-chloropropylamine and the mixture is stirred at room temperature for 1.5 hours. The reaction mixture is poured into iced water and extracted with ethyl acetate. The extract is washed with water and dried over magnesium sulfate and, thereafter, the solvent is distilled off under reduced pressure. An oily product obtained as the residue is subjected to column chromatography on alumina and eluted from the column with a benzenechloroform mixture. The eluate is treated according to usual procedure to obtain an oily 2-(3-dimethylaminopropylthio)-5-(2-chlorophenyl)-7-chloro-3H-1,4-benzodiazepine. The oily product thus obtained is treated, according to usual procedure, with fumaric acid and recrystallized from anhydrous ethanol and acetone to obtain 4.3 g of 2-(3-dimethylaminopropylthio)-5-(2-chlorophenyl)-7- chloro-3H-1,4-benzodiazepine fumarate, m.p. 154°–156° C.

Elementary analysis: for $C_{20}H_{21}N_3Cl_2S \cdot C_4H_4C_4$: Calculated: C: 55.17, H: 4.82, N: 8.04; Found: C: 54.99, H: 4.68, N: 7.93.

EXAMPLE 6

To a solution of 3.2 g of 1,3-dihydro-5-(2-chlorophenyl)-7-chloro-2H-1,4-benzodiazepine-2-thione in a solvent mixture comprising 17 ml of a 10% aqueous potassium hydroxide solution and 1.2 ml of tetrahydrofuran are added at room temperature with stirring 1.75 g of N,N-dimethyl-3-chloropropylamine hydrochloride and 100 mg of benzyltriethylammonium chloride, and the resulting mixture is stirred on a water bath at 40° C. for 4 hours. The reaction mixture is diluted with water and extracted with ethyl acetate. The extract is washed with water and dried over magnesium sulfate and, thereafter, the solvent is distilled off under reduced pressure to obtain an oily 2-(3-dimethylaminopropylthio)-5-(2-chlorophenyl)-7-chloro-3H-1,4-benzodiazepine. The oily product thus obtained is treated, according to usual procedure, with fumaric acid and recrystallized from isopropyl alcohol to obtain 4.40 g of 2-(3-dimethylaminopropylthio)-5-(2-chlorophenyl)-7-chloro-3H-1,4-benzodiazepine fumarate, m.p. 154°–156° C.

EXAMPLES 7

To a solution of 9.6 g of 1,3-dihydro-5-(2-chlorophenyl)-7-chloro-2H-1,4-benzodiazepine-2-thione in a solvent mixture comprising 40 ml of a 10% aqueous sodium hydroxide solution and 40 ml of methanol is added at room temperature 4.4 g of 1-chloro-2-(1-pyrrolidinyl)ethane hydrochloride, and the resulting mixture is stirred at room temperature for 3 hours. The reaction mixture is diluted with water and extracted with ethyl acetate. The extract is washed with water and dried over magnesium sulfate and, thereafter, the solvent is distilled off under reduced pressure to obtain an oily 2-[2-(1-pyrrolidinyl)ethylthio]-5-(2-chlorophenyl)-7-chloro-3H-1,4-benzodiazepine. The oily product thus obtained is treated, according to usual procedure, with fumaric acid and recrystallized from isopropyl alcohol to obtain 6.9 g of 2-[2-(1-pyrrolidinyl)ethylthio]-5-(2-chlorophenyl)-7-chloro-3H-1,4-benzodiazepine fumarate, m.p. 184°–188° C.

Elementary analysis: for $C_{21}H_{21}N_3SCl_2 \cdot C_4H_4O_4$: Calculated: C: 56.18, H: 4.72, N: 7.86; Found: C: 56.15, H: 4.71, N: 7.90.

EXAMPLE 8

To a solution of 9.6 g of 1,3-dihydro-5-(2-chlorophenyl)-7-chloro-2H-1,4-benzodiazepine-2-thione in a solvent mixture comprising 40 ml of a 10% aqueous sodium hydroxide solution and 40 ml of methanol is added dropwise a solution of 5.5 g of 1-chloro-2-piperidinoethane hydrochloride in 20 ml of water over a period of 15 minutes, and the resulting mixture is stirred at room temperature for 3 hours. The reaction mixture is diluted with water and extracted with ethyl acetate. The extract is washed with water and dried over magnesium sulfate and, thereafter, the solvent is distilled off under reduced pressure to obtain an oily 2-(2-piperidinoethylthio)-5-(2-chlorophenyl)-7-chloro-3H-1,4-benzodiazepine. The oily product thus obtained is treated, according to usual procedure, with fumaric acid and recrystallized from 99% ethanol to obtain 10.5 g of 2-(2-piperidinoethylthio)-5-(2-chlorophenyl)-7-chloro-3H-1,4-benzodiazepine fumarate, m.p. 196°–198° C.

Elementary analysis: for $C_{22}H_{23}N_3SCl_2 \cdot C_4H_4O_4$: Calculated: C: 56.93, H: 4.96, N: 7.66; Found: C: 56.93, H: 5.10, N: 7.63.

EXAMPLE 9

To a solution of 7.5 g of 1,3-dihydro-5-(2-chlorophenyl)-7-chloro-2H-1,4-benzodiazepine-2-thione in a solvent mixture comprising 30 ml of a 10% aqueous sodium hydroxide solution and 30 ml of methanol is added dropwise under ice cooling with stirring an aqueous solution of 7.0 g of 1-chloro-2-(perhydroazepin-1-yl)ethane hydrochloride over a period of about 10 minutes, and the resulting mixture is stirred at room temperature for 4 hours. The reaction mixture is diluted with water and extracted with ethyl acetate. The extract is rinsed with a 5% aqueous sodium hydroxide solution, washed with water and dried. Thereafter the solvent is distilled off to obtain an oily residue of 2-(2-perhydroazepin-1-ylethylthio)-5-(2-chlorophenyl)-7-chloro-3H-1,4-benzodiazepine. The oily product thus obtained is treated, according to usual procedure, with 2.74 g of fumaric acid and recrystallized from isopropyl alcohol to obtain 9.9 g of 2-(2-perhydroazepin-1-ylethylthio)-5-(2-chlorophenyl)-7-chloro-3H-1,4-benzodiazepine fumarate, m.p. 170°–171° C.

Elementary analysis: for $C_{23}H_{25}N_3SCl_2 \cdot C_4H_4O_4$: Calculated: C: 57.65, H: 5.20, N: 7.47; Found: C: 57.76, H: 5.31, N: 7.40.

EXAMPLE 10

To a solution of 6.4 g of 1,3-dihydro-5-(2-chlorophenyl)-7-chloro-2H-1,4-benzodiazepine-2-thione in a solvent mixture comprising 34 ml of a 10% aqueous potassium hydroxide and 2.5 ml of tetrahydrofuran is added 4.5 g of 1-chloro-2-morpholinoethane hydrochloride, and the resulting mixture is stirred at room temperature for 3 hours. The reaction mixture is diluted with water and extracted with ethyl acetate. The extract is washed with water, dried over magnesium sulfate and, thereafter, the solvent is distilled off under reduced pressure to obtain an oily 2-(2-morpholinoethylthio)-5-(2-chlorophenyl)-7-chloro-3H-1,4-benzodiazepine. The oily product thus obtained is treated, according to usual procedure, with fumaric acid and recrystallized from isopropyl alcohol to obtain 7.5 g of 2-(2-morpholinoethylthio)-5-(2-chlorophenyl)-7-chloro-3H-1,4-benzodiazepine fumarate, m.p. 191°–193° C.

Elementary analysis: for $C_{21}H_{21}N_3OSCl_2 \cdot C_4H_4O_4$: Calculated: C: 54.55, H: 4.58, N: 7.63; Found: C: 54.40, H: 4.39, N: 7.65.

EXAMPLE 11

To a solution of 11.5 g of 1,3-dihydro-5-(2-chlorophenyl)-7-chloro-2H-1,4-benzodiazepine-2-thione in 100 ml of anhydrous dimethylformamide is added under ice cooling with stirring 2.1 g of sodium hydride (50% oily suspension), and the resulting mixture is stirred at 30° C. for 1 hour. To the mixture is added dropwise a solution of 12.5 g of 1-chloro-3-[4-(2-methoxyphenyl)-1-piperazinyl]propane hydrochloride in 50 ml of dimethylformamide over a period of 15 minutes, and the resulting mixture is stirred at room temperature for 3 hours. The reaction mixture is poured into iced water and extracted with ethyl acetate. The extract is washed with water and dried over magnesium sulfate and, thereafter, the solvent is distilled off under reduced pressure to obtain an oily 2-[3-[4-(2-methoxyphenyl)-1-piperazinyl]-propylthio]-5-(2-chlorophenyl)-7-chloro-3H-1,4-benzodiazepine. The oily product thus obtained is treated, according to usual procedure, with fumaric acid and recrystallized from isopropyl alcohol to obtain 10.5 g of 2-[3-[4-(2-methoxyphenyl)-1-piperazinyl]propylthio]-5-(2-chlorophenyl)-7-chloro-3H-1,4-benzodiazepine fumarate, m.p. 189°–191° C.

Elementary analysis: for $C_{29}H_{30}N_4OSCl_2 \cdot C_4H_4O_4$: Calculated: C: 59.19, H: 5.11, N: 8.36; Found: C: 58.91, H: 5.35, N: 8.15.

EXAMPLE 12

To a solution of 4.4 g of 1,3-dihydro-5-(2-fluorophenyl)-7-bromo-2H-1,4-benzodiazepine-2-thione in a solvent mixture comprising 21.5 ml of a 10% aqueous potassium hydroxide solution and 1.4 ml of tetrahydrofuran is added at room temperature with stirring 2.74 g of N,N-dimethyl-2-chloroethylamine hydrochloride, and the resulting mixture is then stirred at room temperature for 2 hours. The reaction mixture is diluted with an aqueous sodium chloride solution and then extracted with ethyl acetate. The extract is washed with water and dried over magnesium sulfate, and the solvent is removed by distillation under reduced pressure, whereby crude crystalline 2-(2-dimethylaminoethylthio)-5-(2-fluorophenyl)-7-bromo-3H-1,4-benzodiazepine is obtained. Recrystallization from an ether-n-hexane mixture gives 4.05 g of 2-(2-dimethylaminoethylthio)-5-(2-fluorophenyl)-7-bromo-3H-1,4-benzodiazepine, m.p. 105°–107.5° C.

Elementary analysis: for $C_{19}H_{19}N_3SBrF = 420.35$: Calculated: C: 54.29, H: 4.56, N: 10.00, S: 7.63; Found: C: 54.12, H: 4.65, N: 9.93, S: 7.68.

EXAMPLE 13

To a solution of 4.8 g of 1,3-dihydro-5-(2-chlorophenyl)-7-chloro-2H-1,4-benzodiazepine-2-thione in a solvent mixture comprising 28 ml of a 10% aqueous potassium hydroxide solution and 1 ml of tetrahydrofuran is added at room temperature with stirring 3.6 g of N,N-dimethyl-2-chloropropylamine hydrochloride, and the resulting mixture is stirred at room temperature for 2 hours and 30 minutes. The mixture is diluted with a saturated aqueous sodium chloride solution and then extracted with ether. The extract is washed with water and dried, and the solvent is removed by distillation under reduced pressure. An oily product obtained as the residue is subjected to column chromatography on silica gel to obtain 3.9 g of crude 2-(1-methyl-2-dimethylaminoethylthio)-5-(2-chlorophenyl)-7-chloro-3H-1,4-benzodiazepine as free base. The crude product is dissolved in acetone and added with 1.1 g of fumaric acid. The solvent is removed by distillation under reduced pressure to obtain crude 2-(1-methyl-2-dimethylaminoethylthio)-5-(2-chlorophenyl)-7-chloro-3H-1,4-benzodiazepine fumarate. Recrystallization from a mixture of isopropyl alcohol, methyl alcohol and ether gives 4.1 g of 2-(2-dimethylamino-1-methylethylthio)-5-(2-chlorophenyl)-7-chloro-3H-1,4-benzodiazepine fumarate, m.p. 178°–180° C., yield 52.5%.

Elementary analysis: for $C_{20}H_{21}N_3SCl_2 \cdot C_4H_4O_4 = 522.45$: Calculated: C: 55.17, H: 4.82, N: 8.04, S: 6.14; Found: C: 54.97, H: 4.77, N: 7.96, S: 6.14.

EXAMPLE 14

To a solution of 5.7 g of 1,3-dihydro-5-phenyl-7-chloro-2H-1,4-benzodiazepine-2-thione in a solvent mixture comprising 57 ml of a 10% aqueous potassium hydroxide solution and 6 ml of tetrahydrofuran is added at room temperature with stirring 7.0 g of 1-chloro-2-(4-methyl-1-piperazinyl)ethane dihydrochloride, and the resulting mixture is stirred at 40° C. for 4 hours. The reaction mixture is diluted with an aqueous sodium chloride solution and then extracted with ethyl acetate. The extract is washed with water and dried over magnesium sulfate, and the solvent is removed by distillation under reduced pressure. An oily product obtained as the residue is dissolved in ethyl alcohol and added with 3.8 g of fumaric acid, and the solvent is distilled off under reduced pressure to obtain a crystalline product. Recrystallization from tetrahydrofuran to obtain 5.4 g of 2-[2-(4-methyl-1-piperazinyl)ethylthio]-5-phenyl-7-chloro-3H-1,4-benzodiazepine difumarate, m.p. 193°–194° C. (decomposition), yield 42%.

Elementary analysis: For $C_{22}H_{25}N_4SCl \cdot C_8H_8O_8$ $H_2O = 663.14$: Calculated: C: 54.33, H: 5.32, N: 8.45; Found: C: 54.13, H: 5.41, N: 8.12.

EXAMPLE 15

To a solution of 1.6 g of 1,3-dihydro-5-(phenyl)-7-trifluoromethyl-2H-1,4-benzodiazepine-2-thione in a solvent mixture comprising 8.5 ml of a 10% aqueous potassium hydroxide solution and 1.5 ml of tetrahydrofuran is added at room temperature with stirring 1.1 g of 1-chloro-2-piperidinoethane hydrochloride and the resulting mixture is then stirred at 50° C for 4 hours. The reaction mixture is diluted with a saturated aqueous sodium chloride solution and then extracted with ethyl acetate. The extract is washed with water and dried over magnesium sulfate, and the solvent is removed by distillation under reduced pressure. Resulting oily product is converted into the fumarate with 510 mg of fumaric acid. Recrystallization from acetone-ether mixture gives 1.5 g of 2-(2-piperidinoethylthio)-5-phenyl-7-trifluoromethyl-3H-1,4-benzodiazepine fumarate, m.p. 132°–134° C.

Elementary analysis: for $C_{23}H_{24}N_3SF_3 \cdot C_4N_4O_4 = 547.61$: Calculated: C: 59.22, H: 5.15, N: 7.67; Found: C: 58.84, H: 5.30, N: 7.64.

EXAMPLE 16

To a solution of 6.4 g of 1,3-dihydro-5-(2-chlorophenyl)-7-chloro-2H-1,4-benzodiazepine-2-thione in a solvent mixture comprising 34 ml of a 10% aqueous potassium hydroxide solution and 5 ml of tetrahydrofuran is added at room temperature with stirring 4.79 g of 1-chloro-3-(1-pyrrolidinyl)propane hydrochloride and the resulting mixture is then stirred at 50° C for 5 hours. The reaction mixture is diluted with a saturated aqueous sodium chloride solution and then extracted with ethyl acetate. The extract is washed with water and dried over magnesium sulfate, and the solvent is removed by distillation under reduced pressure. Resulting oily product is converted into the fumarate with 2.6 g of fumaric acid. Recrystallization from isopropyl alcohol gives 7.0 g of 2-[3-(1-pyrrolidinyl)propylthio]-5-(2-chlorophenyl)-7-chloro-3H-1,4-benzodiazepine fumarate, m.p. 148°–151° C.

Elementary analysis: for $C_{22}H_{23}N_3SCl_2 \cdot C_4H_4O_4 = 548.51$: Calculated: C: 56.93, H: 4.96, N: 1.66; Found: C: 56.90, H: 4.70, N: 1.92.

EXAMPLE 17

To a solution of 6.4 g of 1,3-dihydro-5-(2-chlorophenyl)-7-chloro-2H-1,4-benzodiazepine-2-thione in a solvent mixture comprising 34 ml of a 10% aqueous potassium hydroxide solution and 5 ml of tetrahydrofuran is added at room temperature with stirring 5.15 g of 1-chloro-3-piperidinopropane hydrochloride and the resulting mixture is then stirred at 50° C for 4 hours. The reaction mixture is diluted with a saturated aqueous sodium chloride solution and then extracted with ethyl acetate. The extract is washed with water and dried over magnesium sulfate, and the solvent is removed by distillation under reduced pressure. Resulting oily product is converted into the fumarate with 2.0 g of fumaric acid. Recrystallization from tetrahydrofuran-ether mixture gives 8.6 g of 2-(3-piperidinopropylthio)-5-(2-chlorophenyl)-7-chloro-3H-1,4-benzodiazepine fumarate, m.p. 110°-112° C.

Elementary analysis: for $C_{23}H_{25}N_3SCl_2 \cdot C_4H_4O_4$ = 562.53: Calculated: C: 57.65, H: 5.20, N: 7.47; Found: C: 58.24, H: 5.74, N: 6.76.

EXAMPLE 18

To a solution of 6.4 g of 1,3-dihydro-5-(2-chlorophenyl)-7-chloro-2H-1,4-benzodiazepine-2-thione in a solvent mixture comprising 34 ml of a 10% aqueous potassium hydroxide solution and 5 ml of tetrahydrofuran is added at room temperature with stirring 5.2 g of 1-chloro-3-morpholinopropane hydrochloride and the resulting mixture is then stirred at 50° C for 2.5 hours. The reaction mixture is diluted with a saturated aqueous sodium chloride solution and then extracted with ethyl acetate. The extract is washed with water and dried over magnesium sulfate, and the solvent is removed by distillation under reduced pressure. Resulting oily product is converted into the fumarate with 2.38 g of fumaric acid. Recrystallization from isopropyl alcohol gives 6.8 g of 2-(3-morpholinopropylthio)-5-(2-chlorophenyl)-7-chloro-3H-1,4-benzodiazepine fumarate, m.p. 169°-171° C.

Elementary analysis: for $C_{22}H_{23}N_3OSCl_2 \cdot C_4H_4O_4$= 564.51: Calculated: C: 55.32, H: 4.82, N: 7.45; Found: C: 55.08, H: 4.79, N: 7.28.

EXAMPLE 19

To a solution of 6.4 g of 1,3-dihydro-5-(2-chlorophenyl)-7-chloro-2H-1,4-benzodiazepine-2-thione in a solvent mixture comprising 34 ml of a 10% aqueous potassium hydroxide solution and 5 ml of tetrahydrofuran is added at room temperature with stirring 5.5 g of 1-chloro-3-(perhydroazepin-1-yl)propane hydrochloride and the resulting mixture is then stirred at 50° C for 4 hours. The reaction mixture is diluted with a saturated aqueous sodium chloride solution and then extracted with ethyl acetate. The extract is washed with water and dried over magnesium sulfate, and the solvent is removed by distillation under reduced pressure. Resulting oily product is converted into the fumarate with 2.8 g of fumaric acid. Recrystallization from tetrahydrofuran-ether mixture gives 9.2 g of 2-(3-perhydroazepin-1-ylpropylthio)-5-(2-chlorophenyl)-7-chloro-3H-1,4-benzodiazepine fumarate, m.p. 164°-167° C.

Elementary analysis: For $C_{24}H_{27}N_3SCl_2 \cdot C_4H_4O_4$ = 576.56: Calculated: C: 58.33, H: 5.42, N: 7.29; Found: C: 58.40, H: 5.44, N: 7.25.

EXAMPLE 20

To a solution of 6.4 g of 1,3-dihydro-5-(2-chlorophenyl)-7-chloro-2H-1,4-benzodiazepine-2-thione in a solvent mixture comprising 20 ml of an aqueous potassium hydroxide solution (prepared by dissolving 2.65 g of potassium hydroxide in water up to 20 ml of the total) and 20 ml of tetrahydrofuran is added at room temperature with stirring 5.0 g of N,N-di-n-hexyl-2-chloroethylamine. After stirring for 2 hours at room temperature, further stirring is made at 50° C for 4 hours. After completion of the reaction, tetrahydrofuran is removed by distillation under reduced pressure and the residue is diluted with water and then extracted with ethyl acetate. The extract is washed with water and dried over magnesium sulfate, and the solvent is removed by distillation. Resulting oily product is converted into the fumarate with 2.3 g of fumaric acid. Recrystallization from ether gives 7.6 g of 2-(2-di-hexylaminoethylthio)-5-(2-chlorophenyl)-7-chloro-3H-1,4-benzodiazepine fumarate, m.p. 113°-115° C.

Elementary analysis: for $C_{29}H_{39}N_3SCl_2 \cdot C_4H_4O_4$ = 648.68: Calculated: C: 61.10, H: 6.68, N: 6.48; Found: C: 61.04, H: 6.67, N: 6.41.

EXAMPLE 21

The following compounds can be obtained in similar manners to those of Examples given above:

1. 2-(10-Dimethylaminodecylthio)-5-(2-chlorophenyl)-7-chloro-3H-1,4-benzodiazepine NMR in $CDCl_3$ δ (ppm)
1.2 – 1.7 (16H, m),
2.18 (6H, s)
2.0 – 2.4 (2H, m)
3.10 (2H, t)
4.20 (2H, s)
7.0 – 7.4 (7H, m)

2. 2-(2-Dimethylaminoethylthio)-5-(2-chlorophenyl)-7-nitro-3H-1,4-benzodiazepine maleate, mp 196° to 198° C.
3. 2-(3-Dimethylaminopropylthio)-5-(2-methoxyphenyl)-7-chloro-3H-1,4-benzodiazepine
4. 2-(4-Dimethylaminobutylthio)-5-(2-chlorophenyl)-7-chloro-3H-1,4-benzodiazepine
5. 2-(6-Dimethylaminohexylthio)-5-(2-chlorophenyl)-7-chloro-3H-1,4-benzodiazepine maleate, mp 108° to 110° C.
6. 2-(2-Dibutylaminoethylthio)-5-(2-chlorophenyl)-7-chloro-3H-1,4-benzodiazepine fumalate, mp 169° to 171° C.
7. 2-[2-[4-hydroxy-4-(4-chlorophenyl)piperidino]ethylthio]-5-(2-chlorophenyl)-7-chloro-3H-1,4-benzodiazepine
8. 2-(2-dimethylaminoethylthio)-5-(2-methoxyphenyl)-8-chloro-3H-1,4-benzodiazepine fumalate, mp 172° to 174° C.
9. 2-(2-diethylaminoethylthio)-5-(2-chlorophenyl)-7-chloro-3H-1,4-benzodiazepine fumalate, mp 158° to 160° C.
10. 2-(2-dimethylaminoethylthio)-5-phenyl-7-chloro-3H-1,4-benzodiazepine fumalate, mp 197° to 199° C.
11. 2-(2-dimethylaminoethylthio)-5-(2-methoxyphenyl)-7-chloro-3H-1,4-benzodiazepine maleate, mp 142° to 145° C.
12. 2-(2-dimethylaminoethylthio)-5-(2-fluorophenyl)-7-nitro-3H-1,4-benzodiazepine fumarate, m.p. 153° to 157° C.
13. 2-(2-dimethylaminoethylthio)-5-(2-fluorophenyl)-7-chloro-3H-1,4-benzodiazepine fumarate, m.p. 164° to 166° C.

14. 2-(2-dimethylaminoethylthio)-5-(2-hydroxyphenyl)-7-chloro-3H-1,4-benzodiazepine (oil), Mass spectrum: m/e 370 (M+).

What is claimed is:

1. A 2-substituted thio-1,4-benzodiazepine compound of the formula

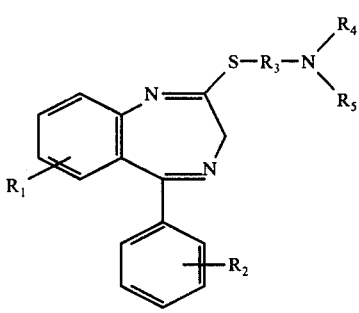

and non-toxic pharmaceutically acceptable salts, wherein $R_1$ is halogen or nitro, $R_2$ is hydrogen, halogen, alkoxy having 1 to 6 carbons or hydroxy, $R_3$ is alkylene having 1 to 10 carbons, and $R_4$ and $R_5$ are alkyl groups having 1 to 6 carbons.

2. The compound according to claim 1, wherein $R_1$ is chlorine, bromine, or nitro, $R_2$ is hydrogen, chlorine, fluorine, methoxy or hydroxy, $R_3$ is ethylene, trimethylene, propylene, tetramethylene, hexamethylene or octamethylene, and $R_4$ and $R_5$ are methyl, butyl or hexyl.

3. The compound according to claim 2, which is 2-(2-dimethylaminoethylthio)-5-phenyl-7-nitro-3H-1,4-benzodiazepine, and its maleate.

4. The compound according to claim 2, which is 2-(2-dimethylaminoethylthio)-5-(2-chlorophenyl)-7-chloro-3H-1,4-benzodiazepine, and its maleate.

5. The compound according to claim 2, which is 2-(3-dimethylaminopropylthio)-5-(2-chlorophenyl)-7-chloro-3H-1,4-benzodiazepine, and its fumarate.

6. The compound according to claim 2, which is 2-(2-dimethylaminoethylthio)-5-(2-fluorophenyl)-7-bromo-3H-1,4-benzodiazepine.

7. The compound according to claim 2, which is 2-(1-methyl-2-dimethylaminoethylthio)-5-(2-chlorophenyl)-7-chloro-3H-1,4-benzodiazepine and its fumarate.

8. The compound according to claim 2, which is 2-(2-dihexylaminoethylthio)-5-(2-chlorophenyl)-7-chloro-3H-1,4-benzodiazepine and its fumarate.

9. The compound according to claim 2, which is 2-(2-dimethylaminoethylthio)-5-(2-chlorophenyl)-7-nitro-3H-1,4-benzodiazepine.

10. The compound according to claim 2, which is 2-(3-dimethylamipropylthio)-5-(2-methoxyphenyl)-7-chloro-3H-1,4-benzodiazepine.

11. The compound according to claim 2, which is 2-(4-dimethylaminobutylthio)-5-(2-chlorophenyl)-7-chloro-3H-1,4-benzodiazepine.

12. The compound according to claim 2, which is 2-(6-dimethylaminohexylthio)-5-(2-chlorophenyl)-7-chloro-3H-1,4-benzodiazepine.

13. The compound according to claim 2, which is 2-(10-dimethylaminodecylthio)-5-(2-chlorophenyl)-7-chloro-3H-1,4-benzodiazepine.

14. The compound according to claim 2, which is 2-(2-dibutylaminoethylthio)-5-(2-chlorophenyl)-7-chloro-3H-1,4-benzodiazepine.

15. The compound according to claim 2, which is 2-(2-dimethylaminoethylthio)-5-(2-methoxyphenyl)-8-chloro-3H-1,4-benzodiazepine and its fumarate.

16. The compound according to claim 2, which is 2-(2-diethylaminoethylthio)-5-(2-chlorophenyl)-7-chloro-3H-1,4-benzodiazepine and its fumalate.

17. The compound according to claim 2, which is 2-(2-dimethylaminoethylthio)-5-phenyl-7-chloro-3H-1,4-benzodiazepine and its fumalate.

18. The compound according to claim 2, which is 2-(2-dimethylaminoethylthio)-5-(2-methoxyphenyl)-7-chloro-3H-1,4-benzodiazepine and its maleate.

19. The compound according to claim 2, which is 2-(2-dimethylaminoethylthio)-5-(2-fluorophenyl)-7-nitro-3H-1,4-benzodiazepine and its fumalate.

20. The compound according to claim 2, which is 2-(2-dimethylaminoethylthio)-5-(2-fluorophenyl)-7-chloro-3H-1,4-benzodiazepine and its fumalate.

21. The compound according to claim 2, which is 2-(2-dimethylaminoethylthio)-5-(2-hydroxyphenyl)-7-chloro-3H-1,4-benzodiazepine.

* * * * *